US00PP35055P2

(12) United States Plant Patent
Hansen

(10) Patent No.: US PP35,055 P2
(45) Date of Patent: Mar. 21, 2023

(54) ***DIANTHUS* PLANT NAMED 'FUNKY FUCHSIA'**

(50) Latin Name: ***Dianthus* hybrid**
Varietal Denomination: Funky Fuchsia

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 17/803,686

(22) Filed: Oct. 13, 2022

(51) Int. Cl.
*A01H 5/02* (2018.01)
*A01H 6/30* (2018.01)

(52) U.S. Cl.
USPC ..... Plt./277

(58) Field of Classification Search
USPC ..... Plt./272, 273, 277, 282
See application file for complete search history.

*Primary Examiner* — Susan McCormick Ewoldt

(57) ABSTRACT

A new and unique plant cultivar of perennial carnation or pinks, *Dianthus* plant named 'Funky Fuchsia' with numerous, large, fully-double, lightly-fragrant flowers producing a rounded full face of solid fuchsia-purple flowers. The flowers are held closely together and cover the top of clump on well-branched sterns having up to 4 flowers per stern beginning in early June and sporadically into fall. The plant is compact with long, thin, bluish-green foliage.

2 Drawing Sheets

Botanical denomination: *Dianthus* hybrid.
Cultivar designation: 'Funky Fuchsia'.

STATEMENT REGARDING PRIOR DISCLOSURES UNDER 37 CFR 1.77(B)(6)

The first non-enabling information of the claimed plant was made on Dec. 1, 2021, in the form of photographs and a brief description on a website operated by Walters Gardens, Inc. and Proven Winners®, followed on Jun. 8, 2022, as a photograph and brief description in the "Walters Gardens 2022-2023 Catalog." Walters Gardens, Inc. obtained the plant and all information relating thereto, from the inventor. The first sales of the new plant were on Jul. 11, 2022, by Walters Gardens, Inc. which obtained the new plant and all information about the new plant from the inventor. No plants of *Dianthus* 'Funky Fuchsia' have been sold, in this country or anywhere in the world, nor has any disclosure of the new plant been made more than one year prior to the filing date of this application, and such sale or disclosure within one year was either derived directly or indirectly from the inventor and would therefore be a 35 U.S.C. § 102b exception.

BACKGROUND OF THE INVENTION

The present invention relates to the new and distinct cultivar of carnation or pinks from the genus *Dianthus* and given the cultivar name 'Funky Fuchsia'. The new plant was the result of an intentional cross on Nov. 17, 2014, under the direction of the inventor, between the unreleased, unnamed, proprietary hybrid known only as 12-64-6 (not patented) as the female or seed parent and the unreleased, unnamed, proprietary hybrid known only as 12-17-1 (not patented as the male or pollen parent. The cross was harvested and sown in the winter of 2014.

The new hybrid was first isolated from trials at a wholesale perennial nursery in Zeeland, Mich. during the summer of 2015 as a single seedling clone and given the breeder number 14-64-1 later in the evaluation processes. *Dianthus* 'Funky Fuchsia' has been asexually propagated at the same nursery in Zeeland, Mich. since 2015 using traditional shoot tip cutting procedures and found to reproduce plants that are identical and exhibit all the characteristics of the original plant.

SUMMARY OF THE INVENTION

*Dianthus* 'Funky Fuchsia' has not been evaluated under all possible environmental conditions. The phenotype may vary with variations in environment including: growing temperature, available sunlight, nutrients, water, etc. without a change in the genotype of the plant.

The female parent, 12-64-6, has flowers of a more reddish-orange. The male parent has flowers of a more mauvy-pink with more deeply toothed petals.

The nearest comparison plants known to the inventor are: 'Cherry Vanilla' U.S. Plant Pat. No. 29,684, 'Cranberry Cocktail' U.S. Plant Pat. No. 28,603, 'Maraschino' U.S. Plant Pat. No. 27,882, and 'Pomegranate Kiss' U.S. Plant Pat. No. 21,895.

'Cherry Vanilla' has smaller flowers with deep red coloring and a very light picotee petal margin. 'Cranberry Cocktail' has large double flowers that are hot magenta-pink. 'Maraschino' has smaller flowers that are bright red with a dark burgundy eye. 'Pomegranate Kiss' has flowers that are deep, velvety red with an irregular splashing of rose-pink.

*Dianthus* 'Funky Fuchsia' is distinct from its parents and all other *Dianthus* known to the applicant in the following combined traits:

1. Fully double flowers opening up with a full and rounded face;
2. Multiple large flowers per stiff, upright peduncle, held closely together having petals with a solid fuchsia-purple coloration and a lightly-sweet spicy fragrance;

3. Flowers cover the complete top of the mound beginning early June and sporadically into fall;
4. Foliage is linear, stiff, bluish-green, on a vigorous, dense habit.

BRIEF DESCRIPTION OF THE DRAWINGS

The photographs of the new invention are of two-year-old plants and demonstrate the overall appearance of the plant including the unique traits. The colors are as accurate as reasonably possible with color reproductions. Some slight variation of color may occur as a result of lighting quality, intensity, wavelength, direction or reflection.

DETAILED DESCRIPTION OF THE PLANT

Figure 1:
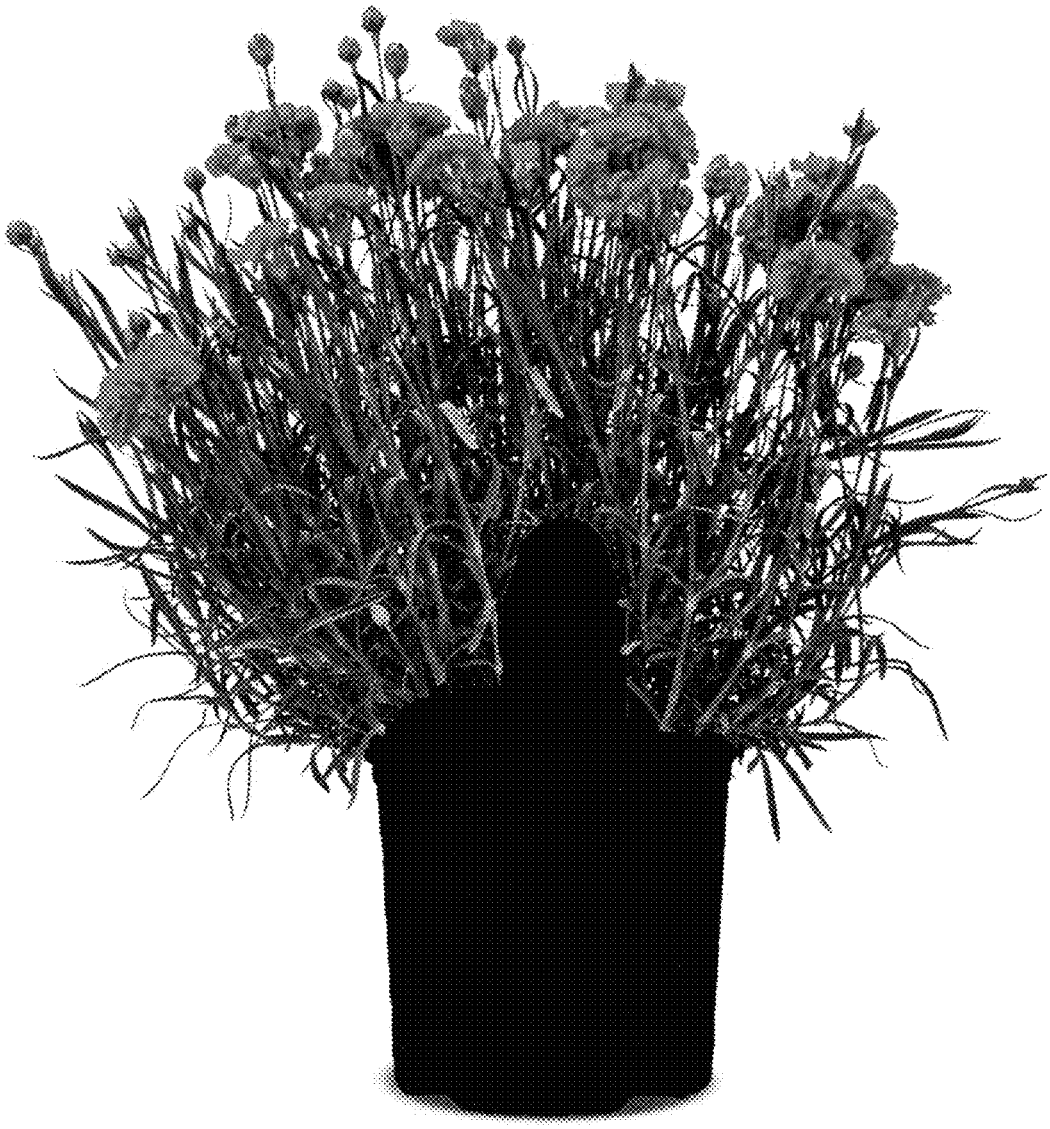
FIG. 1 shows the habit of the plant in mid-season flowering of a greenhouse-grown plant in a container.
Figure 2:
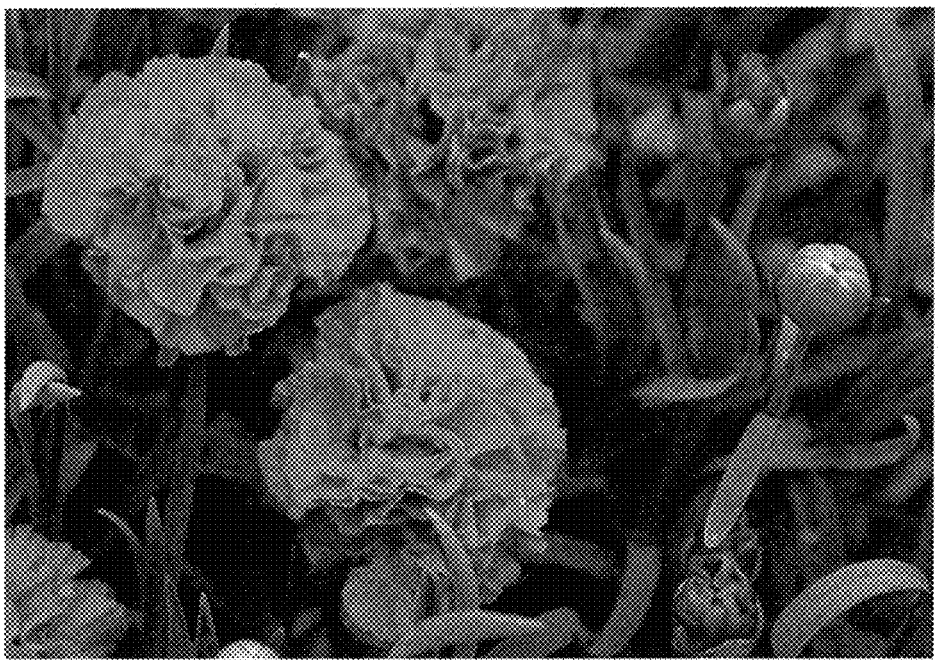
FIG. 2 shows a close-up of the flowers and buds of a plant grown in a full-suntrial garden.

The following detailed description of the new plant is based on observations of one-year-old plants in greenhouse-grown containers in addition to two-year-old plants in full-sun trial garden at a nursery in Zeeland, Mich. with supplemental watering, light additions of fertilizer and free of other plant growth regulators. All color usage is in accordance with the 2015 edition of The Royal Horticultural Colour Chart except where common dictionary terms are used.

Botanical classification: *Dianthus* hybrid;

Parentage: 12-64-6 as the female or seed parent and 12-17-1 as the male or pollen parent;

Plant habit: caespitose, herbaceous, evergreen, winter-hardy perennial; stiff compact foliage; stems and peduncles branched, mostly erect stems; height of foliage about 17 cm and about 35 cm across; height in flower is about 23 cm;

*Root system*.—Fine, fibrous; color nearest RHS 155D depending on soil substrate and nutrition.

*Vigor*.—Good, spring planted plugs finish in 3.8-liter pots in seven to eight weeks.

Foliage:

*Leaf type*.—Simple, linear, opposite, decussate, sessile, glabrous, stiff, strongly glaucous to pruinose both adaxial and abaxial; margin entire to microscopically serrulate; acute apex; base decurrent, adpressed along stem and slightly perfoliate; moderately cupped in longitudinal cross section; no fragrance detected.

*Leaf dimensions*.—To about 78 mm long and about 5 mm wide, average about 66 mm long and 4.5 mm wide.

*Leaf color*.—Young expanding leaves adaxial and abaxial between RHS N138A and RHS 189B; mature adaxial and abaxial between RHS N138A and RHS 189B.

*Venation*.—Not pronounced; obscurely pinnate, coloration same as that of leaf top and bottom.

Stems: Upright; terete, glabrous, glaucous, branching at alternate nodes; solid; about 40 stems per plant;

*Stem size*.—About 6 cm long to peduncle and about 4 mm wide at base.

*Stem color*.—Nearest RHS 189B.

*Branching*.—Numerous; typically alternate, from mostly lower nodes; about 4 per main stem and about 100 per plant; branch size average about 3 cm at time of initial flowering.

*Nodes*.—About 4 mm across opposite leave and 6 mm across with leaves; color nearest RHS 189B.

*Internodes*.—About 8 per stem before peduncle; average about 1 mm apart depending on growing temperature, shorter proximally and in cooler conditions; thickness medium.

Inflorescence:

*Type*.—Terminal, cymose; perfect; salverform; actinomorphic; double.

*Attitude*.—Strongly upright.

*Dimension*.—About 3.3 cm across and extending about 3 cm above base of calyx tube.

*Flowers per stem*.—Up to four, average three.

*Pedicel*.—Glaucous, glabrous, terete, stiff, short.

*Pedicel size*.—Terminal flower about 2 mm long and about 2 mm diameter; other flowers average about 1 mm long and 1.5 mm diameter.

*Pedicel color*.—Nearest RHS 188C.

*Flower bud*.—Slowly opening; glabrous; glaucous; with calyx still closed-ellipsoid with rounded base and acute apex, about 15 mm tall and 11 mm across middle of sepals; with petals extended beyond calyx and still parallel to calyx side: terete, with rounded base and truncate apex or petal tops, about 21 cm tall and 13 mm across at distal fusion point of sepals.

*Flower bud color*.—With petals enclosed in calyx — nearest RHS 138A and distally moderately blushed nearest RHS N186C; with petals extended beyond calyx — petal portion distally nearest RHS N79A and just above calyx nearest RHS N79C.

*Flower period*.—Beginning late spring and continuing for up to four weeks; individual flowers effective about 7 to 10 days.

*Flower fragrance*.—Light, sweet spicy, clove-like.

*Flower lasting quality*.—About six to ten days on or cut from plant.

*Petals*.—Glabrous; up to about 40 per flower; consisting of a rounded blade or limb and a claw; limb and claw combined are flabellate; apex and margin with fine, irregular, shallow dentations typically between 0.5 mm to 1 mm deep; limb bent outwardly in distal 12 mm of perimeter petals to nearly 90° angle creating a full rounded face; limb to about 19 mm across; claw tapering to attenuate base about 0.7 mm across at base; persistent; undulations typically weak in outer petals and moderate to folded in inner petals.

*Petal color*.—Adaxial limb base between RHS NN78D and RHS N78C, distally nearest RHS NN78A, adaxial claw base nearest RHS 145D, mid-claw nearest RHS 145C, distal claw nearest RHS NN155C; abaxial limb base between RHS NN78D and RHS N78C, distal limb nearest RHS 71C; abaxial claw base nearest RHS 145D, mid-claw nearest RHS 145C, distal claw nearest RHS NN155C.

*Petal dimension*.—Overall to about 25 mm long, average about 23 mm long; to about 19 mm across at widest portion of limb, average about 15 mm across; claw to about 0.7 mm wide at base and about 14 mm long, average about 12 mm long.

*Calyx*.—Campanulate; to about 17 mm long and 15 mm across.

*Sepals*.—Five; glabrous; glaucous abaxial; margins entire to micro-puberulent; consisting of five sepals with acute apex, bases fused in the proximal 12 mm; individually about 17 mm long and about 9.0 mm across at distal fusion.

*Sepal color*.—Adaxial distal margin nearest RHS 165A, remaining proximal portion nearest RHS 145C; abaxial distal portion nearest RHS 165A and proximally nearest RHS 138B.

*Peduncle*.—Glabrous, glaucous, terete, stiff; about 6 cm long and about 3 mm diameter at base; attitude mostly upright.

*Peduncle color*.—Nearest RHS 190B.

*Epicalyx*.—Two pairs; opposite, glaucous, glabrous; sessile, margin entire, broadly ovate with broadly acute apex and rounded base; outer pair about 5 mm long and about 5 mm wide, inner pair about 7 mm long and about 9 mm across.

*Epicalyx color*.—Both pairs abaxial and adaxial marginal portion translucent to nearest RHS NN155B and proximally variable between RHS 138A and RHS 146D.

*Androecium*.—Variable number between zero and thirteen stamens, typically not all fully formed, to some staminode petals or without anthers. Filaments: when present — to about 15 mm long, about 0.5 mm diameter; color in basal three-quarters white, lighter than RHS NN155D, distally becoming nearest RHS 75A; Anther: when present — oblong, dorsifixed; to about 2 mm long and about 1 mm wide; color with longitudinal portions nearest RHS 79B and RHS N75A; Pollen: not observed.

*Gynoecium*.—Single. Style: bifurcate just above ovary; glabrous abaxial and becoming puberulent in adaxial distal 15 mm, total 16 mm long; color nearest RHS 72A distally, and nearest RHS NN155C proximally; Stigma: slightly flattened abaxial to adaxial; puberulent adaxial; about 1 mm long and 1 mm wide; color nearest RHS N186B; Ovary: superior; ellipsoidal with broadly acute apex and truncate base; about 6 mm long and 5 mm wide; surface smooth; color nearest RHS 146D distally and RHS 145D proximally.

Fruit and seed: Not observed; possibly sterile or recalcitrant;

Disease resistance: The new plant is resistant to center die out from fungus or high temperatures.

Garden performance: The plant grows best with adequate moisture and well-drained soil but is able to tolerate some drought once established. Hardiness at least from USDA zone 4 through zone 9.

It is claimed:

1. A new and distinct *Dianthus* plant named 'Funky Fuchsia' essentially as herein described and illustrated.

* * * * *